United States Patent
Scherer et al.

(10) Patent No.: US 6,891,060 B2
(45) Date of Patent: May 10, 2005

(54) PREPARATION OF 3-ACYLOXY-2-METHYLBENZOIC ACIDS

(75) Inventors: Johannes Scherer, Leverkusen (DE); Horst Behre, Odenthal (DE); Friedrich Müller-Hauck, Bendorf (DE)

(73) Assignee: BayerAktiengesellschaft, Leverkusen (DE)

( * ) Notice: Subject to any disclaimer, the term of this patent is extended or adjusted under 35 U.S.C. 154(b) by 70 days.

(21) Appl. No.: 10/458,093

(22) Filed: Jun. 10, 2003

(65) Prior Publication Data

US 2004/0044243 A1 Mar. 4, 2004

(30) Foreign Application Priority Data

Jun. 13, 2002 (DE) ......................................... 102 26 219

(51) Int. Cl.[7] ............................................... C07C 69/00
(52) U.S. Cl. ...................................................... 560/130
(58) Field of Search ......................................... 560/130

(56) References Cited

U.S. PATENT DOCUMENTS

| 5,484,926 A | 1/1996 | Dressman et al. | 546/114 |
| 5,527,829 A | 6/1996 | Kalish | 514/604 |
| 6,051,732 A | 4/2000 | Cosmo et al. | 891/130 |

FOREIGN PATENT DOCUMENTS

DE 91201 C 2/1897

*Primary Examiner*—Paul J. Killos
(74) *Attorney, Agent, or Firm*—Diderico van Eyl; Godfried R. Akorli

(57) ABSTRACT

The invention relates to an improved process for preparing 3-acyloxy-2-methylbenzoic acids by heating substituted naphthalenes in the presence of alkali metal hydroxides and subsequently acylating.

15 Claims, No Drawings

PREPARATION OF 3-ACYLOXY-2-METHYLBENZOIC ACIDS

BACKGROUND OF THE INVENTION

1. Field of the Invention

The invention relates to an improved process for preparing 3-acyloxy-2-methylbenzoic acids by heating substituted naphthalenes in the presence of alkali metal hydroxides and subsequently acylating.

2. Brief Description of the Prior Art

3-Acyloxy-2-methylbenzoic acids, for example 3-acetoxy-2-methylbenzoic acid, are valuable intermediates in the preparation of pharmaceuticals, for example HIV protease inhibitors (see, for example, U.S. Pat. No. 5,484,926) and agrochemicals.

EP-A 891 964 discloses a process for preparing such compounds which starts from 3-amino-1,5-naphthalenedisulphonic acid or its alkali metal salts and proceeds via the reaction with alkali metal hydroxide, removal of insolubles and reaction with acetic anhydride.

A disadvantage of this process is the use of the expensive 3-amino-1,5-naphthalenedisulphonic acid or its salts and also the unsatisfactory overall yield of 60%.

There is therefore a need to develop an efficient process which enables the preparation of 3-acyloxy-2-methylbenzoic acids in an advantageous manner.

SUMMARY OF THE INVENTION

A process has now been found for preparing compounds of the formula (I)

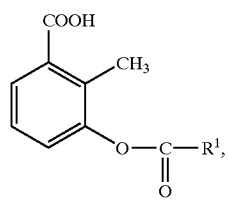

(I)

where $R^1$ is $C_1$–$C_{20}$-alkyl, $C_7$–$C_{20}$-arylalkyl, $C_{13}$–$C_{20}$-diarylalkyl or radicals of the formulae (IIa) or (IIb)

A-OR² (IIa)

A-NR³R⁴ (IIb)

where A is in each case a $C_1$–$C_4$-alkylene radical and $R^2$ and also $R^3$ and $R^4$ are each independently methyl, ethyl and isopropyl, which is characterized in that
a) compounds of the formula (III)

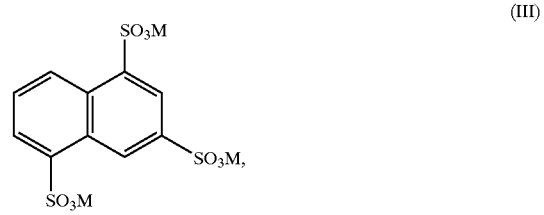

(III)

where M is in each case independently hydrogen, ammonium, an alkali metal or half of an equivalent of an alkaline earth metal, are reacted with alkali metal hydroxide and optionally alkaline earth metal hydroxide in the presence of water and b) the reaction mixtures (obtained in step a),
   optionally after addition of water and
   optionally after removal of insoluble constituents and
   optionally after the separation of undesired, soluble constituents,
are partially neutralized and c) the reaction mixtures obtained in step b) are reacted with compounds of the formulae (IVa) or (IVb)

R¹—COX (IVa)

(R¹—CO)₂O (IVb)

where the $R^1$ radicals are in each case independently as defined above and d) the reaction mixtures obtained in step c) are acidified.

For the purposes of the invention, alkyl and alkylene are each independently a straight-chain, cyclic, branched or unbranched alkyl and alkylene radical respectively. The same applies to the alkylene moiety of an aralkyl radical.

DETAILED DESCRIPTION OF THE INVENTION

In all contexts, $C_1$–$C_{20}$-alkyl is, for example, preferably methyl, ethyl, n-propyl, isopropyl, n-butyl, tert-butyl, n-pentyl, cyclohexyl, n-hexyl, n-heptyl, n-octyl, isooctyl, n-decyl, n-dodecyl, n-hexadecyl and n-octadecyl.

In all contexts, $C_1$–$C_4$-alkylene is, for example, preferably methylene, 1,1-ethylene, 1,2-ethylene, 1,1-propylene, 1,2-propylene, 1,3-propylene, 1,1-butylene, 1,2-butylene, 2,3-butylene and 1,4-butylene.

For the purposes of the invention, arylalkyl is, for example and with preference, an alkyl radical which is substituted by carbocyclic aromatic radicals having 6 to 10 carbon atoms, in particular phenyl and naphthyl, and the carbocyclic aromatic radicals may themselves be substituted by up to five substituents per cycle which are selected from the group of methyl, ethyl, fluorine, chlorine, bromine and $C_1$–$C_4$-fluoroalkyl where fluoroalkyl is an alkyl radical as defined above which is singly, multiply or fully substituted by fluorine. The same applies to the aryl moiety of a diarylalkyl radical.

In particular, $C_1$–$C_4$-fluoroalkyl is trifluoromethyl, pentafluoroethyl, 2,2,2-trifluoroethyl and nonafluorobutyl.

Particular preference is given to using 1,3,5-naphthalenetrisulphonic acid and its mono-, di- or trialkali metal salts for step a).

Very particular preference is given to using the trialkali metal salts of 1,3,5-naphthalenesulphonic acid, for example trisodium 1,3,5-naphthalenetrisulphonate and tripotassium 1,3,5-naphthalenetrisulphonate, and even greater preference is given to trisodium 1,3,5-naphthalenetrisulphonate.

Some of the compounds of the formula (III) can occur in the form of hydrates which are not mentioned specifically, but are encompassed by the invention.

The compounds of the formula (III) are either commercially available, or can be prepared by literature procedures or in a similar manner.

In a preferred embodiment of the process according to the invention, the naphthalene 1,3,5-trisulphonic acid or its mono-, di- or trialkali metal salts are prepared in such a way that i) naphthalene is reacted with fuming sulphuric acid to give naphthalene-1,3,5-trisulphonic acid and ii) the naphthalene 1,3,5-trisulphonic acid obtained in step i) is optionally converted using an alkali metal base to a mono-, di- or trialkali metal salt.

At this point, it is pointed out that any desired combination of the features and of the areas of preference specified are likewise encompassed by the invention.

Step i) can advantageously be effected by reacting naphthalene with fuming sulphuric acid.

An example of a possible procedure is to initially charge fuming sulphuric acid and add naphthalene or initially charge concentrated sulphuric acid and naphthalene and add fuming sulphuric acid, or initially charge concentrated sulphuric acid and add naphthalene and fuming sulphuric acid.

The preferred procedure in step i) is to initially charge concentrated sulphuric acid and add naphthalene and fuming sulphuric acid.

For the purposes of the invention, concentrated sulphuric acid is, for example, sulphuric acid comprising 90 to 100% by weight of $H_2SO_4$. For the purposes of the invention, fuming sulphuric acid is sulphuric acid which has a content of over 100% by weight, based on pure $H_2SO_4$. Another common term for fuming sulphuric acid for the purposes of the invention is oleum.

Typically, the content of free $SO_3$ in commercially available oleum is specified and is, for example, 30 or 65% by weight.

Preference is given to using such an amount of oleum in step a) that the molar ratio of free $SO_3$ to naphthalene is between 1.5:1 and 10:1, preferably between 2:1 and 5:1 and more preferably between 2.5:1 and 4:1.

The temperature in the course of addition can be, for example, −20 to 70° C., preferably 20 to 55° C.

The time for the addition can be, for example, between 10 min and 48 h, preferably 2 to 24 hours.

Subsequently, the resulting reaction mixture can optionally be heated. The temperature can be, for example, between 55 and 150° C., preferably between 80 and 100° C.

The naphthalene 1,3,5-trisulphonic acid can be recovered from the resulting reaction mixture, for example, by adding water.

Alkali metal or alkaline earth metal salts of naphthalene-1,3,5-trisulphonic acid can be prepared according to step ii) either from the isolated naphthalene-1,3,5-trisulphonic acid or directly from the reaction mixture resulting from step i). Preference is given to the preparation of alkali metal or alkaline earth metal salts of naphthalene-1,3,5-trisulphonic acid from the reaction mixture resulting from step i).

Step ii) can be effected, for example, in such a way that the reaction mixture resulting from step i) is diluted, for example, by pouring into water or onto ice, and subsequently reacted with alkali metal hydroxides, hydrogencarbonates or carbonates or aqueous solutions thereof.

Preference is given to using alkali metal hydroxides, in particular sodium hydroxide and potassium hydroxide, or aqueous solutions thereof.

Particular preference is given to the reaction with aqueous solutions of sodium hydroxide.

The alkali metal hydroxide content of the solutions can be, for example, between 2 and 75% by weight, preferably from 25 to 60% by weight.

The temperature of the reaction for step ii) can be, for example, 0 to 100° C., preferably 80 to 100° C.

The amount of alkali metal hydroxide used can be, for example, 2 to 10 times, based on the molar ratio of the naphthalene used in step i), preferably 2.8 to 3.5 times.

After workup in a manner known per se, which can be effected, for example, by filtration and optionally washing and drying the precipitated solid, alkali metal salts of naphthalene-1,3,5-trisulphonic acid are obtained which are either stored or preferably reacted further.

Optionally, the alkali metal salt of naphthalene-1,3,5-trisulphonic acid obtained in step ii) may be still further purified, for example, by recrystallization, although this is unnecessary for use in step a) of the process according to the invention.

In step a) of the process according to the invention, the compounds of the formula (III) are reacted with alkali metal hydroxide and optionally alkaline earth metal hydroxide in the presence of water.

The alkali metal hydroxide used may be, for example and with preference, sodium hydroxide or potassium hydroxide or a mixture thereof, for example as a solid or in the form of an aqueous solution.

The amount of alkali metal hydroxide for step a) may be selected, for example, in such a way that 6 to 40 mol, preferably from 8 to 25 mol, of alkali metal hydroxide are used per mole of compound of the formula (III).

Alkaline earth metal hydroxides can preferably also be added. Examples of suitable alkaline earth metal hydroxides are magnesium hydroxide and calcium hydroxide, although preference is given to calcium hydroxide.

The amount of alkaline earth metal hydroxide for step a) may, for example, be selected in such a way that 0.5 to 30 mol, preferably 2 to 20 mol, more preferably 2 to 15 mol and most preferably 2.0 to 3.1 mol, of alkaline earth metal hydroxide are used per mole of compound of the formula (III).

The molar ratio of water to the compound of the formula (III) can be, for example, 0.5 to 200 mol, preferably 3 to 50 mol.

In a particularly preferred embodiment, the ratio of water to the sum of alkali metal hydroxide and any alkaline earth metal hydroxide added is 1:1.4 to 1:6.0.

The pressure in the reaction can be, for example, 1 to 200 bar, preferably 1 to 100 bar, more preferably 10 to 60 bar and most preferably that pressure which results from heating the reaction mixture to the reaction temperature in a closed vessel starting from ambient temperature.

An example of a useful closed vessel is an autoclave which can be made, for example, of nickel, nickel-based alloys, silver or other, alkali-resistant material.

The temperature of the reaction can be, for example, 240 to 350° C., preferably 270 to 320° C.

The reaction time can be, for example, 2 to 25 hours, preferably 3 to 8 hours.

In step b) of the process according to the invention, the reaction mixtures obtained in step a) are at least partially neutralized with acid, optionally after adding water and optionally after the removal of insoluble constituents and optionally the removal of undesired, soluble constituents.

In a preferred embodiment, water is optionally added after cooling the reaction mixture, which can be effected, for example, by pouring the reaction mixture into water or onto ice.

Preference is also given to removing insoluble constituents. This may be effected, for example and with preference, by filtration, centrifugation, sedimentation and decanting, optionally in the presence of assistants. Examples of possible assistants include kieselguhr, for example Celite®, activated carbon, for example Norite®, bleaching earth, montmorillonite or animal charcoal. Preference is given to filtration, particular preference to filtration in the presence of assistants, preferably activated carbon.

Preference is likewise given to the removal of undesired, soluble constituents. Without making any claim to completeness, undesired, soluble constituents are, for example, coloured organic by-products. The removal of undesired, soluble constituents may be carried out, for example, before or after the at least partial neutralization. An example of a possible procedure is to extract with organic solvent. Examples of suitable organic solvents are esters such as ethyl acetate and butyl acetate, aliphatic or aromatic, optionally halogenated hydrocarbons, for example petroleum, benzene, toluene, xylenes, chlorobenzene, dichlorobenzenes, isopropylbenzene, petroleum ether, hexane, heptane, octane, isooctane, cyclohexane, methylcyclohexane, dichloromethane, chloroform or carbon tetrachloride; ethers such as diethyl ether, methyl tert-butyl ether or diisopropyl ether, ketones such as 2-butanone or methyl isobutyl ketone or mixtures of such solvents.

The reaction mixture may also, for example, be freed of discolorations using a suitable adsorbent. Examples of suitable adsorbents include silica gels, aluminium oxides, cellulose or activated carbon.

When removing undesired, soluble constituents, the pH can be, for example, 4 to 13, preferably 6.5 to 11.5. In the case of pH values below 7.5, base may be added again before step c) is carried out, in order to attain the preferred pH range in step a).

The partial neutralization is preferably effected by setting to a pH of 7.5 to 13, preferably 9.5 to 11.5. The pH values relate to values at 25° C. For partial neutralization, preference is given to using acids or acidic salts having a pKa in water of 5 or less. For partial neutralization, preference is given to using sulphuric acid, hydrochloric acid, phosphoric acid, nitric acid and hydrobromic acid, particular preference is given to using sulphuric acid and hydrochloric acid, and very particular preference to using sulphuric acid.

In a very particularly preferred embodiment, step b) is carried out in such a way that the reaction mixture obtained from step a) is initially diluted with water, insolubles are removed, undesired, soluble constituents are removed and the pH is set to 7.5 to 13.

In step c), the reaction mixture from step b) is reacted with compounds of the formulae (IVa) or (IVb).

In the compounds of the formulae (IVa), $R^1$ is preferably methyl, ethyl, n-propyl, isopropyl, tert-butyl or benzyl, particularly preferably methyl, and X is chlorine, bromine or iodine.

A particularly preferred compound of the formula (IVa) is acetyl chloride.

In the compounds of the formulae (IVb), $R^1$ is in each case independently, but preferably identically, methyl, ethyl, n-propyl, isopropyl or benzyl, more preferably methyl.

A particularly preferred compound of the formula (IVa) which is particularly preferred for the process according to the invention is acetic anhydride.

The amount of compound of the formula (IVa) or (IVb) is, for example and with preference, selected in such a way that the molar ratio to the compound of the formula (II) originally used is 0.8:1 to 10:1, preferably 1:1 to 5:1.

The reaction temperature in step c) is, for example, −10 to 120° C., preferably −10 to 100° C. and more preferably 50 to 100° C.

The reaction pressure for step c) is not critical, although preference is given to ambient pressure.

The reaction time for step c) can be, for example, 1 to 25 hours, preferably 2 to 10 hours.

Preference is further given to maintaining the pH in the course of the reaction between 7.5 and 13, preferably 9.5 and 11.5, which can be effected, for example, by adding base.

Useful bases are in particular alkali metal hydroxides, carbonates or hydrogen-carbonates, although preference is given to sodium hydroxide and potassium hydroxide. The base can be used, for example, in solid form or in the form of aqueous solutions.

Subsequently, in step d), the reaction mixture obtained in step c) is acidified. Preference is given to acidifying to a pH of 3.5 or less, more preferably to 0 to 3.5, and most preferably to 1 to 2.5.

Examples of useful acidifiers include acids or acidic salts having a pKa in water of 3.5 or less, preferably 0 or less. Particular preference is given to sulphuric acid or hydrochloric acid.

In a preferred embodiment of step d), initial acidification is effected only to a pH of above 3.5 and below 8, and undesired, soluble constituents are extractively removed as described above. Subsequently, the reaction mixture may then, for example, be freed of discolorations using a suitable adsorbent. Examples of useful adsorbents include silica gels, aluminum oxides, cellulose or activated carbon.

Subsequently, the mixture is further acidified.

The temperature on acidifying is not critical, although it may be advantageous to heat the reaction mixture to boiling, in order to drive out dissolved gases or decompose any sulphites present. The acidification protonates the mono- or disalts of the compounds of the formula (I) and at least partly converts them to the free acids of the formula (I).

The compounds of the formula (I) may be obtained in a manner known per se from the reaction mixtures obtained in step d), for example by extraction with organic solvent, filtration, centrifugation or sedimentation and decanting.

Examples of preferred solvents for the extraction are esters such as ethyl acetate and butyl acetate, aliphatic or aromatic, optionally halogenated hydrocarbons, for example petroleum, benzene, toluene, xylenes, chlorobenzene, dichlorobenzenes, isopropylbenzene, petroleum ether, hexane, heptane, octane, isooctane, cyclohexane, methylcyclohexane, dichloromethane, chloroform or carbon tetrachloride; ethers such as diethyl ether, methyl tert-butyl ether or diisopropyl ether, ketones such as 2-butanone or methyl isobutyl ketone or mixtures of such solvents.

The compounds of the formula (I) may be obtained after extraction in a manner known per se, for example by evaporating the solvent.

When the compounds of the formula (I) are removed by filtration, centrifugation or sedimentation and decanting, this may be effected, for example and with preference, at −20 to 70° C., more preferably 5 to 55° C.

For further purification, the compounds of the formula (I) may optionally be recrystallized or reprecipitated, although this is unnecessary.

The compounds of the formula (I) prepared by the process according to the invention, in particular 3-acetoxy-2- methylbenzoic acid, are particularly suitable for use in a process for preparing pharmaceuticals, for example HIV protease inhibitors, and agrochemicals, for example crop protection agents and insecticides, or intermediates thereof, in particular the acid chlorides or acid bromides.

The compounds of the formula (I) are also suitable for preparing the analogous activated acid derivatives, in particular the acid chlorides and acid bromides.

The advantage of the processes according to the invention is the efficient preparation of compounds of the formula (I), which enables them to be carried out in high yields without costly and inconvenient intermediate isolation.

EXAMPLES

Example 1

In a nickel autoclave, 300.0 g of trisodium 1,3,5-naphthalenetrisulphonate (70.9%, determined as the free acid) are stirred into a mixture of 232.0 g of aqueous sodium hydroxide solution (45%) and 194.0 g of sodium hydroxide in such a way that a readily stirrable, pasty suspension is obtained. The autoclave is closed and heated to 280° C. The internal pressure (autogenous pressure) rises to 18.4 bar. The mixture is stirred at reaction temperature for a further 6 hours and is cooled afterwards to 90° C. At this temperature, 200.0 g of water are pumped in and the mixture is cooled afterwards to room temperature. The suspension obtained is filtered with suction and washed with 187.3 g of water. 251.8 g of a brownish-white, finely divided solid and 795.7 g of a dark brown solution are obtained.

Example 2

A flask is initially charged with 390.0 g of the solution from Example 1. 20.0 g of activated carbon are added and the pH is set to 7.0 by metering in hydrochloric acid (37%), the mixture is heated to reflux, the reaction solution is clarified and washed with water. The clarified reaction solution is returned to the flask, cooled to 0° C. and set to pH 9.6 by metering in sodium hydroxide solution (30%). Acetic anhydride and sodium hydroxide solution are now metered in simultaneously at 0 to 5° C. in such a way that the pH remains in the range from 9.3 to 9.7. Within 1 hour, 39.8 g of acetic anhydride and 75.9 g of sodium hydroxide solution (30%) are metered in. Afterwards, stirring is continued at the same temperature for 0.5 hour. Afterwards, the pH is set to 1 at 5° C. by adding hydrochloric acid. The product precipitates out as a white precipitate. The product is filtered off with suction on a glass suction filter and washed with water. The precipitate is dried in a vacuum drying cabinet. 38.7 g of 3-acetoxy-2-methylbenzoic acid (purity 95.0%) are obtained. This corresponds to an isolated yield based on trisodium 1,3,5-naphthalenetrisulphonate of 67% of theory.

Example 3

In a nickel autoclave, 300.0 g of trisodium 1,3,5-naphthalenetrisulphonate (70.9%, determined as the free acid) are stirred into a mixture of 356.0 g of aqueous sodium hydroxide solution (45%) and 126.0 g of sodium hydroxide pastilles and 127.0 g of calcium hydroxide in such a way that a readily stirrable, pasty suspension is obtained. The autoclave is closed and heated to 310° C. The internal pressure (autogeneous pressure) rises to 50 bar. The mixture is stirred at reaction temperature for a further 5 hours and is cooled afterwards to 90° C. At this temperature, 200.0 g of water are pumped in and the mixture is cooled afterwards to room temperature. The suspension obtained is filtered with suction and washed with 609.6 g of water. 295.0 g of a brownish-white, finely divided solid and 1388.8 g of a dark brown solution are obtained.

Example 4

A flask is initially charged with 300.0 g of the solution from Example 3. 5 g of activated carbon are added and the pH is set to 7.0 by metering in hydrochloric acid (37%), the mixture is heated to reflux, the reaction solution is clarified and washed with water. The clarified reaction solution is returned to the flask, cooled to 0° C. and set to pH 9.6 by metering in sodium hydroxide solution (30%). Acetic anhydride and sodium hydroxide solution are now metered in simultaneously at 0 to 5° C. in such a way that the pH remains in the range from 9.3 to 9.7. Within 1 hour, 14.8 g of acetic anhydride and 22.3 g of sodium hydroxide solution (30%) are metered in. Afterwards, stirring is continued at the same temperature for 0.5 hour. Afterwards, the pH is set to 1 at 5° C. by adding hydrochloric acid. The product precipitates out as a white precipitate. The product is filtered off with suction on a glass suction filter and washed with water. The precipitate is dried in a vacuum drying cabinet. 17.4 g of 3-acetoxy-2-methylbenzoic acid (purity 98.2%) are obtained. This corresponds to an isolated yield based on trisodium 1,3,5-naphthalenetrisulphonate of 71% of theory.

Example 5

3-acetoxy-2-methylbenzoic Acid

In a flat-flanged vessel, 80.0 g of 3-hydroxy-2-methylbenzoic acid (purity 97.78%) are dissolved in 320.0 g of water and 120.0 g of sodium hydroxide solution (w=30%), which results in a pH of 6.9. The clear solution is cooled to 0° C. and adjusted to pH=9 by metering in sodium hydroxide solution (w=30%). Acetic anhydride and sodium hydroxide solution are now simultaneously metered in at 0–5° C. in such a way that the pH remains within the range of 8.8–9.2. 112.6 g of acetic anhydride and 172.25 g of sodium hydroxide solution (w=30%) are metered in within 2.5 h. Afterwards, the mixture is stirred for a further 1.5 h. A second flat-flanged vessel is charged with 150.0 g of water and cooled to 0° C. The reaction mixture of the first vessel and hydrochloric acid (w=37%) are simultaneously metered in at a maximum of 5° C. in such a way that a pH of 3.8–4.2 is maintained. The product precipitates out as a white precipitate. The pH is adjusted to 1 by metering in hydrochloric acid (w=37%). The product is filtered off with suction and washed with 500.0 g of water. The precipitate is dried in a vacuum drying cabinet at 60° C. for 16 h. 172.6 g of 3-acetoxy-2-methylbenzoic acid (purity 99.9%) are obtained. This corresponds to 99.28% of theory.

Example 6

3-acetoxy-2-methylbenzoyl Chloride

A flask is initially charged with 100.0 g of thionyl chloride under nitrogen and heated to 60° C. A melt at 170° C. of 100.0 g of 3-acetoxy-2-methylbenzoic acid (AMBA) is added dropwise within one hour. The reaction commences immediately with evolution of gas ($SO_2$, HCl). After the addition is complete, the mixture is heated to reflux (80° C.) over one hour and stirred at this temperature until the gas evolution subsides (approx. 1 h). The solution is cooled to approx. 50° C. under nitrogen and the reflux condenser is replaced by a Vigreux column. 31.9 g of thionyl chloride are distilled off at atmospheric pressure (liquid phase up to 170°

C.) and the remaining liquid phase is fractionated under reduced pressure (15 mbar). The distillate obtained is 103.8 g of 3-acetoxy-2-methylbenzoyl chloride (98.5%). This corresponds to 95.5% of theory.

Example 7

3-acetoxy-2-methylbenzoyl Chloride

In a flask, 60.0 g of 3-acetoxy-2-methylbenzoic acid are suspended under nitrogen in 140.0 g of xylene. The suspension is heated to 70° C. and 42.9 g of thionyl chloride are added dropwise. The mixture is heated further. At approx. 75° C., vigorous gas evolution ($SO_2$, HCl) commences. The liquid phase temperature rises continuously and reaches 108° C. after approx. 4 h. The solution is cooled to approx. 50° C. under nitrogen and the reflux condenser is replaced by Vigreux column. At atmospheric pressure and later under reduced pressure, first xylene and thionyl chloride residues and then the product are distilled over. The product distills over at 15 mbar and 147.0–148.0° C. 59.6 g of 3-acetoxy-2-methylbenzoyl chloride (97.3%) are obtained. This corresponds to 91.0% of theory.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing compounds of the formula (I)

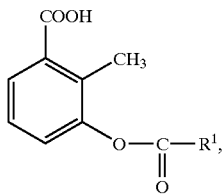

(I)

where
$R^1$ is $C_1$–$C_{20}$-alkyl, $C_7$–$C_{20}$-arylalkyl, $C_{13}$–$C_{20}$-diarylalkyl or radicals of the formulae (IIa) or (IIb)

A—$OR^2$ (IIa)

A—$NR^3R^4$ (IIb)

where A is in each case a $C_1$–$C_4$-alkylene radical and $R^2$ and also $R^3$ and $R^4$ are each independently methyl, ethyl and isopropyl,
comprising reacting
a) compounds of the formula (III)

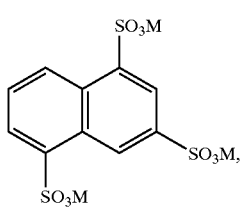

(III)

where M is in each case independently hydrogen, ammonium, an alkali metal or half of an equivalent of an alkaline earth metal, with alkali metal hydroxide in the presence of water and b) partially neutralizing the reaction mixtures obtained in step a) and c) reacting the reaction mixtures obtained in step b) with compounds of the formulae (IVa) or (IVb)

$R^1$—COX (IVa)

$(R^1$—$CO)_2O$ (IVb)

where the $R^1$ radicals are in each case independently as defined above and d) acidifying the reaction mixtures obtained in step c).

2. Process according to claim 1, characterized in that step a) is carried out in the presence of alkaline earth metal hydroxide.

3. Process according to claim 1, characterized in that step a) is carried out in the presence of calcium hydroxide.

4. Process according to claim 1, characterized in that, in step a), 1,3,5-naphthalenetrisulphonic acid or its mono-, di- or trialkali metal salts are used.

5. Process according to claim 1, characterized in that trisodium 1,3,5-naphthalenetrisulphonate is used in step a).

6. Process according to claim 1, characterized in that, in step b), partial neutralization is effected after addition of water.

7. Process according to claim 1, characterized in that, in step b), insoluble constituents are removed by filtration, centrifugation or sedimentation and decanting.

8. Process according to claim 1, characterized in that, in step b), undesired, soluble constituents are removed by extraction.

9. Process according to claim 1, characterized in that, in step b), the pH is adjusted to 7.5 to 13.

10. Process according to claim 1, characterized in that acetic anhydride is used in step c).

11. Process according to claim 1, characterized in that, in step c), the molar ratio of compound of the formula (IVa) or (IVb) to the compound of the formula (II) used is 0.8:1 to 10:1.

12. Process according to claim 1, characterized in that, in step c), the pH is maintained between 7.5 and 13 in the course of the reaction.

13. Process according to claim 1, characterized in that, in step d), acidification is effected to a pH of 3.5 or less.

14. Process according to claim 13, characterized in that, in step d), initial acidification is effected to a pH above 3.5 and below 8 and undesired, soluble constituents are extractively removed and the reaction mixture is then further acidified.

15. Process according to claim 1, characterized in that the compounds of the formula (I) are obtained by extraction with organic solvent, filtration, centrifugation or sedimentation and decanting.

* * * * *